(12) United States Patent
Sofranko

(10) Patent No.: US 10,710,040 B2
(45) Date of Patent: *Jul. 14, 2020

(54) SYSTEMS FOR PROMOTING ENDOTHERMIC CONVERSIONS WITH OXYGEN TRANSFER AGENTS

(71) Applicant: EcoCatalytic Inc., Monmouth Junction, NJ (US)

(72) Inventor: John A. Sofranko, Princeton, NJ (US)

(73) Assignee: EcoCatalytic Inc., Woburn, MA (US)

(*) Notice: Subject to any disclaimer, the term of this patent is extended or adjusted under 35 U.S.C. 154(b) by 0 days.

This patent is subject to a terminal disclaimer.

(21) Appl. No.: 16/400,842

(22) Filed: May 1, 2019

(65) Prior Publication Data
US 2019/0255500 A1 Aug. 22, 2019

Related U.S. Application Data

(63) Continuation of application No. 15/738,212, filed as application No. PCT/US2016/038512 on Jun. 21, 2016, now Pat. No. 10,322,392.
(Continued)

(51) Int. Cl.
*B01J 8/02* (2006.01)
*B01J 8/18* (2006.01)
(Continued)

(52) U.S. Cl.
CPC ............. *B01J 8/0285* (2013.01); *B01J 8/02* (2013.01); *B01J 8/025* (2013.01); *B01J 8/0278* (2013.01);
(Continued)

(58) Field of Classification Search
None
See application file for complete search history.

(56) References Cited

U.S. PATENT DOCUMENTS 2,867,677 A * 1/1959 Murray .................... C07C 5/46
 585/442
3,420,912 A 1/1969 Woskow et al.
(Continued)

FOREIGN PATENT DOCUMENTS

FR 2158365 A1 * 6/1973 ............. B01J 27/04
GB 2050188 A * 1/1981 .......... B01J 27/1853
WO 2016049144 A1 3/2016

OTHER PUBLICATIONS

Machine translation of FR 2158365 A1 (Jun. 1973). Retrieved from Espacenet on Jul. 27, 2019. (Year: 2019).*
(Continued)

*Primary Examiner* — Jennifer A Leung
(74) *Attorney, Agent, or Firm* — RatnerPrestia

(57) ABSTRACT

A system for promoting endothermic conversions includes a first and second portion, a first and second supply, a first outlet, and a heat exchanger. The first portion defines a first inner volume containing an oxygen transfer agent. The first supply contains a reducing agent and is fluidly connected to the first inner volume. The first outlet conveys one or more of carbon dioxide, water, and an unsaturated hydrocarbon from the first inner volume. The second portion and the heat exchanger positioned within the second portion define a second inner volume containing reduced oxygen transfer agent. The second supply contains an oxidizing agent fluidly connected to the second inner volume. The heat exchanger also defines a third inner volume segregated from the second inner volume, and the heat exchanger is configured to transfer heat resulting from the oxidation of the reduced oxygen transfer agent to the third inner volume.

12 Claims, 3 Drawing Sheets

Related U.S. Application Data

(60) Provisional application No. 62/183,048, filed on Jun. 22, 2015, provisional application No. 62/184,620, filed on Jun. 25, 2015.

(51) Int. Cl.
    *C07C 5/48*     (2006.01)
    *B01J 8/08*     (2006.01)
    *B01J 8/12*     (2006.01)
    *B01J 19/24*     (2006.01)
    *B01J 23/34*     (2006.01)

(52) U.S. Cl.
    CPC ............... *B01J 8/085* (2013.01); *B01J 8/087* (2013.01); *B01J 8/12* (2013.01); *B01J 8/18* (2013.01); *B01J 8/1836* (2013.01); *B01J 8/1863* (2013.01); *B01J 19/243* (2013.01); *B01J 23/34* (2013.01); *C07C 5/48* (2013.01); *B01J 2208/00115* (2013.01); *B01J 2208/00141* (2013.01); *B01J 2208/00309* (2013.01); *B01J 2219/00117* (2013.01); *C07C 2523/34* (2013.01); *Y02P 20/52* (2015.11)

(56) References Cited

U.S. PATENT DOCUMENTS

| | | | | |
|---|---|---|---|---|
| 3,585,249 | A | * | 6/1971 | Abraham .................. C07C 5/46 585/433 |
| 3,666,687 | A | * | 5/1972 | Croce ...................... B01J 21/10 502/220 |
| 4,511,754 | A | | 4/1985 | Gaffney et al. |
| 4,634,802 | A | | 1/1987 | Jones et al. |
| 5,118,898 | A | | 6/1992 | Tyler et al. |
| 5,691,262 | A | | 11/1997 | Hagemeyer et al. |
| 5,866,737 | A | | 2/1999 | Hagemeyer et al. |
| 8,196,532 | B2 | | 6/2012 | Andrus et al. |
| 10,322,392 | B2 | * | 6/2019 | Sofranko ............... B01J 8/1863 |
| 2004/0010174 | A1 | | 1/2004 | Wang et al. |
| 2011/0117004 | A1 | | 5/2011 | Lamont et al. |
| 2014/0275679 | A1 | | 9/2014 | Sofranko |
| 2014/0377158 | A1 | | 12/2014 | Andrus et al. |

OTHER PUBLICATIONS

Alstom—Chemical Looping Combustion Prototype—2 pages.
Andrus, H., "Alstom Response to Technical Reviewers' Comments on NDIC Proposal", Nov. 14, 2013—40 pages.
Bailie et al.,"Potential Advantages of Incineration in Fluidized Beds", 1968 National Incinerator Conference—pp. 12-17.
Beal et al., "Alstom Chemical Looping Technologies Status", 2nd International Oxyfuel Combustion Conference,—4 pages.
Brzic et al., "An Experiment Study of the Partial Oxidation of Ethane to Ethylene in a Shallow Fluidized Bed Reactor", J. Serb. Chem. Soc., 72(2), pp. 183-192 (2007).
Chiu et al., "Alstom's Chemical Looping Technology Program Update", 2014 USDOE/NETL, CO2 Capture Technology Meeting, Jul. 29 to Aug. 1, 2014, Pittsburgh, PA—32 pages.
Fan et al., "Chemical Looping Technology Platform", AIChE Journal Perspective Article, Sep. 19, 2014—62 pages.
International Preliminary Report on Patentability for International Application PCT/US2016/038512, dated Dec. 26, 2017—8 pages.
International Search Report and Written Opinion for International Application No. PCT/US2016/038512, dated Aug. 29, 2016—11 pages.
Pécora et al., "Heat Transfer Coefficient in a Shallow Fluidized Bed Heat Exchanger with a Continuous Flow of Solid Particles", J. of the Braz. Soc. of Mech. Sci. & Eng., Jul.-Sep. 2006, vol. XXVII, No. 3—pp. 253-258.
Process Economics Program Report 248, "Steam Cracking for Olefins Production," PEP '03 MAC, Jul. 2003 (Abstract)—8 pages.
Roy et al., "Fluidized Bed Heat Transfer", Chemical Processing & Engineering, Feb. 1970—pp. 17-24.
Stevanovic et al., "Pebble-Heater Technology in Metallurgy", Association of Metallurgical Engineers of Serbia & Montenegro—18 pages.
Stevanovic et al., "Pebble-Heater Twins with Fluid Dynamic Valve—An Efficient Possibility for High Combustion Air Preheating",—10 pages.
U.S. Dept. of Energy, "Development, Validation and Application of CFD-Based Models for Describing Chemical Looping Processes", R&D Facts, Office of Fossil Energy, National Energy Technology Laboratory, Oct. 2006—2 pages.
Yamaguchi et al., "Small Scale Hydrogen Production from Metal-Metal Oxide Redox Cycles", Hydrogen Energy-Challenges and Perspectives, Chapter 2—pp. 31-54, 2012.

\* cited by examiner

SYSTEMS FOR PROMOTING ENDOTHERMIC CONVERSIONS WITH OXYGEN TRANSFER AGENTS

CROSS-REFERENCE TO RELATED APPLICATIONS

The present application is a continuation of U.S. application Ser. No. 15/738,212, filed Dec. 20, 2017, which is a U.S. national phase application of PCT International Application PCT/US2016/038512, filed Jun. 21, 2016, and claims the benefit of priority to U.S. Provisional Application Nos. 62/183,048, entitled COUPLING OF EXOTHERMIC AND ENDOTHERMIC REACTIONS IN HYDROCARBON DEHYDROGENATION VIA CHEMICAL LOOPING, and 62/184,620, entitled HEAT TRANSFER AGENTS FOR OXIDATIVE DEHYDROGENATION OF HYDROCARBONS, filed on Jun. 22, 2015 and Jun. 25, 2015, respectively, the contents of which are incorporated herein by reference in their entireties for all purposes.

FIELD OF THE INVENTION

The invention relates to reactor systems and processes that utilize oxygen transfer agents for the oxidative dehydrogenation (ODH) of hydrocarbons, specifically oxygen transfer agents and blends thereof having a high thermal effusivity.

BACKGROUND OF THE INVENTION

Ethylene and propylene are important building blocks for the petrochemical industry. These olefins are used in the manufacturing of polymers such as polyethylene, polypropylene, polystyrene and many more chemicals of commercial interest. Over 90% of the global olefin production comes from the high temperature steam cracking of naphtha or ethane and propane. The steam cracking process, which utilizes furnaces, is highly energy intensive, and 1.5 to 2 tons of carbon dioxide is produced for every ton of olefin product.

Natural gas production from shale deposits has dramatically increased supply in recent years. As a result of the continued global demand for olefins and the potential for a new growing supply of ethane and propane available in natural gas liquids from shale deposits, a significant amount of interest and investment is currently centered around expanding the capacity of ethylene and propylene derived from these new sources. Numerous olefin grass root and expansion projects are either under contract or in the planning stages to take advantage of the relative low cost liquids from wet shale gas. However, there are many environmental and cost challenges to bringing on this level of new capacity.

Olefin production is the largest emitter of $CO_2$ and NOR in the organic chemical industry. With worldwide ethylene production at ~150 MT/yr, the industry emits 150-300 MT/yr of $CO_2$ and roughly 1.4 MT/yr of NOR. Projects located in severe EPA non-attainment zones are challenged by the increased cost of NOx control. The total greenhouse gas (GHG) emission profile, reported in $CO_2$ equivalents, is another critical part of the permitting for all production expansions.

The industry continues to push for production technology that: (1) generates higher overall yield of ethylene and propylene; (2) increases the run length between furnace turnarounds (e.g. inspections, repairs, improvements, etc.); (3) lowers steam and energy utilization; and (4) lowers all GHGs including carbon dioxide and NOR. ODH of ethane and propane offers a potential solution for these needs.

The ODH of ethane and propane to olefins offers a production route that can significantly reduce $CO_2$ emissions and virtually eliminate NOR emissions from world scale plants. ODH is a selective catalytic process that produces primarily ethylene and water as products, and is thereby an exothermic reaction (reaction 1).

$$CH_3CH_3 + \tfrac{1}{2} O_2 \rightarrow CH_2CH_2 + H_2O \quad \Delta H_o = -105 \text{ kJ/mol} \quad (1)$$

The per pass yield of the ODH reaction is not limited by thermodynamic equilibrium, as it is in pyrolysis, (reaction 2).

$$CH_3CH_3 + \text{Heat} \leftrightarrows CH_2CH_2 + H_2 \quad \Delta H_o = +137 \text{ kJ/mol} \quad (2)$$

ODH provides an opportunity to achieve some of the objectives to improve the efficiency of olefin production. Therefore, there is a need for improved reactors and processes for facilitating efficient ODH conversions.

SUMMARY OF THE INVENTION

It is a first aspect of the present invention to provide a system for promoting endothermic conversions. The system may comprise a first and second portion, a first and second supply, and a heat exchanger positioned within the second portion. The first portion may define a first inner volume at least partially filled with an oxygen transfer agent. The first supply may contain one or more of hydrogen and a saturated hydrocarbon fluidly connected to a first inlet of the first inner volume. The second supply may contain an oxidizing agent fluidly connected to a second inlet to the second inner volume. The system may further comprise a first outlet for conveying one or more of carbon dioxide, water, and an unsaturated hydrocarbon from the first inner volume. The second portion and the heat exchanger may define a second inner volume at least partially filled with reduced oxygen transfer agent The heat exchanger may also define a third inner volume segregated from the second inner volume and be configured to transfer heat resulting from the oxidation of the reduced oxygen transfer agent in the second inner volume to the third inner volume.

It is another aspect of the present invention to provide a method of promoting endothermic conversions. The method may comprise contacting a saturated hydrocarbon with an oxygen transfer agent resulting in a reduced oxygen transfer agent and an unsaturated hydrocarbon, contacting the reduced oxygen transfer agent with an oxidizing agent resulting in an exothermic reaction, and transferring heat from the exothermic reaction to a heat exchanger to promote an endothermic conversion within the heat exchanger. The heat exchanger may be positioned within a vessel and the vessel and the heat exchanger may define a first inner volume at least partially filled with the reduced oxygen transfer agent, and the heat exchanger may define a second inner volume segregated from the first inner volume.

BRIEF DESCRIPTION OF THE FIGURES

In order that the invention may be more fully understood, the following figures are provided by way of illustration, in which.

DETAILED DESCRIPTION OF THE INVENTION

Figure 1:
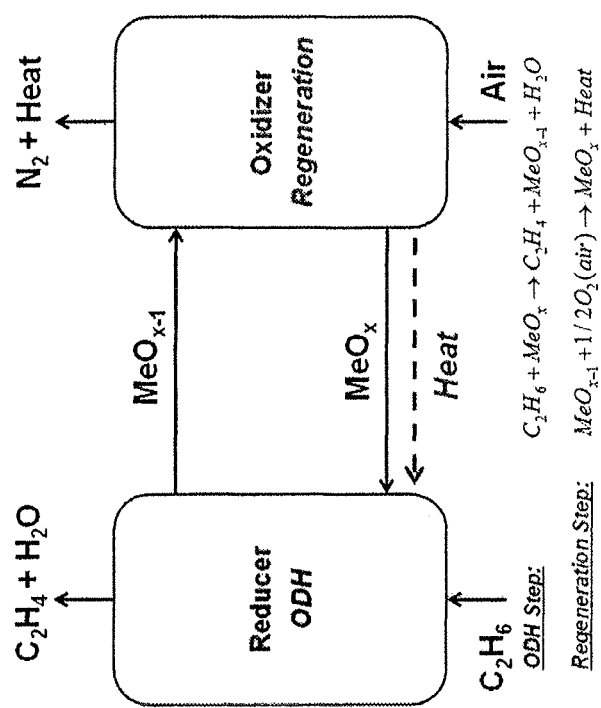
FIG. 1 is a schematic of an ODH Chemical Looping Mechanism utilizing an oxygen transfer agent.

Although the invention is illustrated and described herein with reference to specific embodiments, the invention is not intended to be limited to the details shown. Rather, various modifications may be made in the details within the scope and range of equivalents of the claims and without departing from the invention.

It is a first aspect of the present invention to provide a system that utilizes the exothermic heat of reaction, enthalpy, from an ODH process in an integrated process in order to maximize the overall energy efficiency of the process. As examples, the heat of reaction may be used to heat up feeds to reaction temperature and/or generate steam for driving compressors or turbines for electricity generation. Another aspect of the present invention provides a system wherein the exothermic heat of reaction from the oxidation of a reduced oxygen transfer agent may be used to promote an endothermic reaction. By efficiently utilizing the exothermic heat of reaction from the oxidation of a reduced oxygen transfer agent, the release of GHG that would typically occur from the burning of fossil fuels for promoting endothermic reactions may be avoided.

The embodiments of the present invention eliminate or reduce the emission of carbon dioxide and nitrogen oxide by-products by relying on "flameless" combustion or oxidation using the unique properties of many solid oxide transfer agents (M) shown in equations (3) and (4), $$M + \tfrac{1}{2} O_2 \rightarrow MO \tag{3}$$

$$MO + Reductant \rightarrow M + Products + H_2O \tag{4}$$

In equation (4), the reductant is converted to products and water. In reactors and processes according to the present invention, it is preferred that the heat released, enthalpy of reaction (3), is larger than the heat required for reaction (4). It is further preferred that the solid oxide transfer agents used for flameless combustion in the various embodiments of the present invention have high heats of reaction, are able to transfer a high percent of the oxide weight to oxygen upon reduction, and have high thermal and physical stability to preserve the activity of the metal/metal oxide and reduce particle attrition in moving or fluid bed applications. Examples of solid oxide transfer agents that may be used in the reactors and processes according to the various embodiments of the present invention are found in Table 1.

TABLE 1

| Oxide Transfer Agent | Reduced form | Wt. % releasable oxygen | ΔHo for reaction (3) kJ/mol |
|---|---|---|---|
| Fe$_2$O$_3$ | Fe | 30.1 | −1,652 |
| MnO$_2$ | MnO | 18.40 | −269.6 |
| CuO | Cu | 20.1 | −314.6 |

The systems and processes according to the embodiments of the present invention may be configured to use the exothermic heat of reaction from an ODH process to promote an endothermic chemical conversion. The solid oxide transfer agents of the systems and processes of the present invention preferably have high transferable oxygen content and significant heat release when they are oxidized from their reduced form. To facilitate heat release, the solids should have high heat capacity and the ability to transfer their heat energy to the environment at high rates, i.e., a high Thermal Effusivity. Thermal Effusivity ("e") is the product of a material's volumetric heat capacity ("Cp") and its thermal conductivity ("k"), taken to the 0.5 power, equation (5).

$$e = (k\rho C_p)^{0.5} \tag{5}$$

Thus, Thermal Effusivity of a material is a measure of its ability to change the thermal energy in its environment. An illustrative list of the thermal effusivity of a few materials is provided in Table 2.

TABLE 2

Thermal Effusivity Examples

| Material | Material Density Kg/m$^3$ | Specfic Heat Capacity J/Kg-K | Thermal Conductivity W/m-K | Thermal Effusivity W·s$^{0.5}$/m$^2$-K |
|---|---|---|---|---|
| magnesium oxide (mgo) (polyxtal, 100 d) | 3580 | 921 | 61.923 | 14285 |
| manganese oxide (mn3o4) (87 pc dense) | 4200 | 628 | 4.184 | 3321 |
| iron oxide (fe2o3) (hematite) | 5240 | 628 | 12.552 | 6425 |
| copper oxide (cuo) (tenorite) | 6500 | 536 | 17.991 | 7914 |
| aluminum oxide (al2o3) (polyxtal 100 d) | 3980 | 778 | 38.493 | 10919 |
| aluminum | 2698 | 921 | 225.94 | 23688 |
| silica glass, fused or vitrous | 2200 | 745 | 1.381 | 1504 |
| silicon carbide (sic) (kt grade) | 3100 | 678 | 179.91 | 19443 |
| copper | 8940 | 385 | 397.48 | 36983 |
| tantalum carbide + wc cermet k601 | 15300 | 209 | 66.944 | 14638 |
| tungsten carbide cermet k94 and k1 | 14100 | 209 | 91.63 | 16440 |
| zinc-aluminum alloy astm 23 | 6600 | 418 | 112.97 | 17662 |
| zinc-aluminum-copper alloy astm 25 | 6700 | 418 | 108.78 | 17463 |

It is preferred that the solid oxygen transfer agents used in the systems and processes of the present invention have thermal effusivities of at least 3,500 and, more preferably, at least 10,000 W·s$^{0.5}$/m$^2$-K. In another embodiment, oxygen transfer agents incorporated in the systems and processes of the present invention may comprise one or more oxygen transfer agents having a high thermal effusivity and an oxygen transfer agent that is highly active and selective for ODH. For example in one embodiment, a system may include a blend of oxygen transfer agents comprising manganese, alkali metals, and tungsten carbide.

Oxygen transfer agents that are highly active and selective for ODH may include materials used for the ODH of hydrocarbons following the generalized formula of Equation 6:

$$zC_nH_{2n+2-2\beta} + (z-1+\delta)\text{"O"} \rightarrow C_{(z \times n)}H_{2(2 \times n)+2-2\beta-2\delta} + (z-1+\delta)H_2O \tag{6}$$

where z=the number of reacting molecules; n=the number of atomic units in the reacting molecule; β=the degree of unsaturation where the value is zero for single bonds, one for double bonds and molecular rings, and two for triple bonds; and δ=the change in the degree of unsaturation. The oxygen, "O" in Equation 6 may be supplied by the reduction of a metal oxide or via the catalytic use of molecular oxygen.

The oxygen transfer agents may also be useful for the case of Equation 6, where the carbon number, n, is equal to one. In this case the useful reaction promoted by these agents is called the oxidative coupling of methane (OCM) to higher hydrocarbons.

A few examples of the reactions described by Equation 6 that may be promoted using an oxygen transfer agent according to the present invention are shown in Table 3.

TABLE 3

| Starting Molecule, CnHy | Number of starting molecules = z | Cn Starting material | Degree unsaturation in starting molecule = β | Change of unsaturation in product = α | Moles of water | Moles of oxygen ($O_2$) | Cn Product | Hn Product | Product Formula | Product Name |
|---|---|---|---|---|---|---|---|---|---|---|
| $CH_4$ | 6 | 1 | 0 | 4 | 9 | 4.5 | 6 | 6 | $C_6H_6$ | Benzene |
| $C_3H_8$ | 2 | 3 | 0 | 1 | 2 | 1 | 6 | 12 | $C_6H_{12}$ | Hexene |
| $C_2H_6$ | 2 | 1 | 0 | 2 | 3 | 1.5 | 4 | 6 | $C_4H_6$ | Butyne |
| $CH_4$ | 2 | 3 | 0 | 1 | 2 | 1 | 2 | 4 | $C_2H_4$ | Ethylene |
| $C_4H_8$ | 1 | 2 | 1 | 1 | 1 | 0.5 | 4 | 6 | $C_4H_6$ | Butyne |
| $C_3H_6$ | 2 | 1 | 1 | 2 | 3 | 1.5 | 6 | 8 | $C_6H_8$ | Cyclohexadiene |
| $CH_4$ | 2 | 4 | 0 | 0 | 1 | 0.5 | 2 | 6 | $CH_3CH_3$ | Ethane |
| $CH_3CH_3$ | 1 | 3 | 0 | 1 | 1 | 0.5 | 2 | 4 | $CH_2CH_2$ | Ethylene |

While promoting the conversion of hydrocarbons according to a reaction according to Equation (6), the oxygen transfer agent is reduced from an oxidized state to a less oxidized, i.e. reduced, state. In order to regenerate the agent, oxygen may be used to re-oxidize the reduced agent. This re-oxidation process may occur concurrent with the reduction of the oxygen transfer agent in the presence of one or more oxidation agent(s) such as oxygen, air, carbon dioxide, steam, NOx, and/or oxides of sulfur. A preferred embodiment of this invention is the re-oxidation of the oxygen transfer agents in a separate step. This reduction/oxidation of the oxygen transfer agent with concurrent formation of useful products, which is schematically illustrated in FIG. 1, is often described as a redox or chemical looping system.

There are many benefits of processing the ODH reaction in a chemical looping mode which include:
- Ability to use inexpensive air vs. expensive oxygen via air separation equipment.
- Heat balance and temperature control of reactor system via the circulation of high heat capacity solids, allowing a self-sustainable operation from an energy balance standpoint.
- Ability to separate the oxidation of the hydrocarbon from the re-oxidation of the oxygen transfer agent, thereby allowing for separate reaction conditions of temperature and pressure for the two different steps.
- Higher selectivity and yield to the desired products of Equation 1, with minimization of unwanted products, such as carbon oxides, than observed when the oxidation is carried out over a catalyst in a co-feed of hydrocarbon and oxygen. The presence of the oxygen transfer agent also drives the dehydrogenation equilibrium towards the product side.
- Use of highly efficient, high through-put reactor systems.
- Near zero emission of both carbon dioxide, sulfur oxides and nitrogen oxides.
- Near zero coke accumulation on the oxygen transfer agent.

In a preferred embodiment of the present invention, a solid oxygen transfer agent is comprised of a mixed oxide preferably with Mixed Ionic Electronic Conductivity (MIEC). MIEC materials useful in this invention promote Equation 6 at high rates and selectivities to the desired ODH products with minimal production of unwanted products such as carbon oxides or coke. The MIEC may have a strong ability to carry the reactive oxygen moiety ("O") into the reactor to perform a reaction according to Equation (6), and also be facile for the reaction to regain its active state. The solid oxygen transfer may also have a high Thermal Effusivity, so that the heat generated by the material from a reaction according to Equation (4) may be used to drive an endothermic reaction according to Equation (3). Examples of MIEC materials that may be used in the systems and processes according to the various embodiments of the present invention are disclosed in International Patent Publication WO 2016/049144 A1, the contents of which are incorporated herein by reference.

The oxygen transfer agents used in the systems and processes according to the various embodiments of the present invention may further include a promoter that serve to promote higher selectivity to specific desired products. While not wishing to be bound to theory, it is believed that active oxygen is drawn to the promoter sites within the oxygen transfer agent. This enables the oxygen transfer agents to act as a selective promoter of a reaction according to Equation (6) and as an oxygen reservoir to the selective promoting agent.

The oxygen transfer agents according to the present invention may be porous, or dense, in so much as effective mass transport of reactants is maintained. The contact time of the feed hydrocarbons or the feed oxidant, typically air, with the oxygen transfer agent may be 0.01 seconds to 60 seconds, when calculated at reaction conditions of temperature and pressure. More typically, the contact time will be in the range of 0.1 to 20 seconds. The reaction contact times are optimized to produce the highest yield of the desired product of oxidation.

The conventional manufacturing process for ethylene, steam cracking, requires a high amount of heat to drive the endothermic cracking of ethane to ethylene and hydrogen, as shown in Equation 7, Table 4.

TABLE 4

Relevant Thermodynamic Values

| Reaction | $\Delta H^{1,100K}$ kJ/mol* | $\Delta G^{1,100K}$ kJ/mol* |
|---|---|---|
| 7) $CH_3CH_3 \rightarrow CH_2CH_2 + H_2$ | 143 | −4.9 |
| 8) $CH_4 + 2 O_2 \rightarrow CO_2 + 2 H_2O$ | −802 | −800 |
| 9) $CH_3CH_3 + \frac{1}{2} O_2 \rightarrow CH_2CH_2 + H_2O$ | −105 | −192 |
| 10) $CH_3CH_3 + 3\frac{1}{2} O_2 \rightarrow 2 CO_2 + 3 H_2O$ | −1429 | −1485 |
| 11) $3 MnO + O_2 \rightarrow Mn_3O_4$ | −223 | −99.3 |
| 12) $H_2 + \frac{1}{2} O_2 \rightarrow H_2O$ | −248 | −187 |
| 13) $Mn_3O_4 + H_2 \rightarrow 3 MnO + H_2O$ | | |
| 14) $CH_3CH_3 + Mn_3O_4 \rightarrow CH_2CH_2 + H_2O + MnO$ | 118 | −92.6 |

In principle, oxygen may be reacted directly with ethane to produce ethylene in an oxy-pyrolysis reaction (Equation (9) in Table 4). However, high yields of ethylene compete with the thermodynamically and kinetically favored product, carbon dioxide (Equation (8) in Table 4).

The selective oxidation of hydrocarbons to olefins, such as ethane to ethylene, may be promoted in a chemical looping sequence, according to reactions (15) and (16) and shown in FIG. 1.

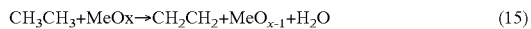
$$CH_3CH_3 + MeO_x \rightarrow CH_2CH_2 + MeO_{x-1} + H_2O \tag{15}$$

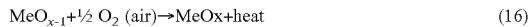
$$MeO_{x-1} + \tfrac{1}{2} O_2 \text{ (air)} \rightarrow MeO_x + \text{heat} \tag{16}$$

Systems according to various embodiments of the present invention may be configured as a chemical looping system comprising an oxygen transfer agent having an exothermic heat of reaction when it is oxidized and an endothermic heat of reaction when it is reduced. For example referring to Table 4, manganese oxide if used as an oxygen transfer agent would provide an endothermic heat of reaction when converting ethane to ethylene (Equation 14); however, re-generating the manganese oxide of oxygen would provide an exothermic heat of reaction (Equation 11).

As noted above, it is an aspect of the present invention to provide systems and processes that will improve the heat management and overall yield of an ODH reaction. It is preferred that the oxygen transfer agents used in the systems and processes of the present invention are capable of selectively promoting a reaction according to Equation (6), have an exothermic heat of oxidation, and a heat of reduction that is less exothermic than the heat of oxidation, more preferably, a heat of reduction that is endothermic. The reactors and processes according to the present invention may be configured as fixed or circulating bed reactors. In the case of fixed bed reactors, multiple reactors may be used such that hydrocarbon oxidation and oxygen transfer agent re-oxidation are occurring continuously as feed and air is alternately cycled to various reactors. Circulating bed reactors in systems according to the present invention may circulate solids from a hydrocarbon reactor zone to an oxygen transfer agent regeneration zone, such as a Mars-van Krevelen-like mechanism, as illustrated in FIG. 1. Such systems would require means for transferring the reduced and re-generated oxygen transfer agents between the zones, such as fluidized, ebullating, or entrained beds, as well as other means known by those of skill in the art. The circulation of the solid oxygen transfer agent may be co-current or counter current to the gas feed to the vessel.

Figure 2A:
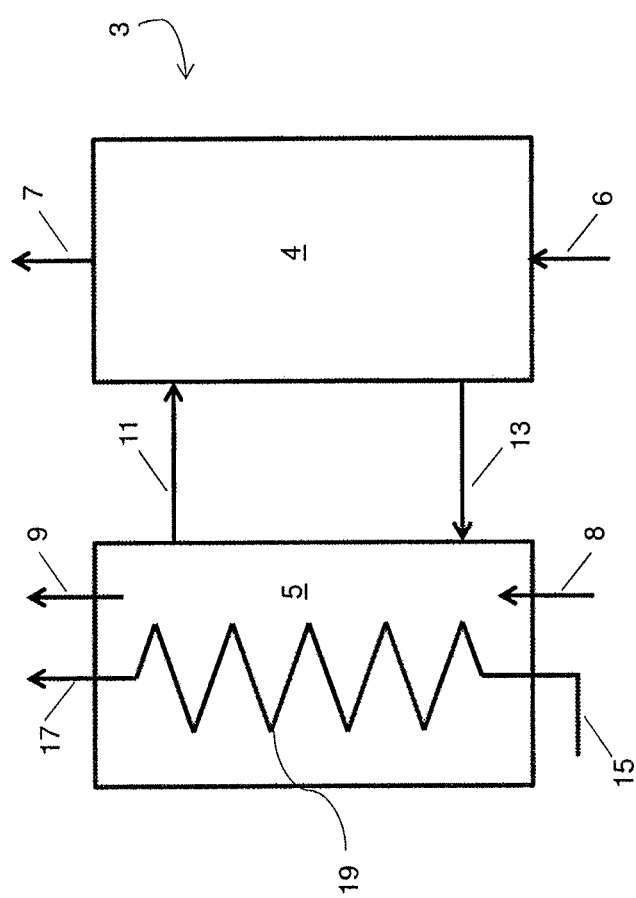
FIG. 2A is a schematic of a circulating bed reactor system according to one embodiment of the present invention.

A circulating bed system 3 according to an embodiment of the present invention is shown in FIG. 2A. A reduction zone 4 is at least partially filled with an oxygen transfer agent (not shown). A reductant, such as hydrogen and/or a saturated hydrocarbon, such as ethane, is fed through inlet 6 into the reduction zone 4 causing reduction of the oxygen transfer agents upon contacting the reductant. Products leaving outlet 7 from the reduction zone 4 may include at least one of water, carbon dioxide, or unsaturated hydrocarbons, such as ethylene. The solid oxygen transfer agent in reduction zone 4 preferably has a high selectivity preference for being reduced by hydrogen, so that the reductant supplied in inlet 6 to the reduction zone may be methane, ethane or other saturated hydrocarbons that can form useful products such as ethylene, propylene and other unsaturated hydrocarbons with low carbon dioxide production.

The reduced oxygen transfer agents are conveyed via line 13 to the oxidation zone 5 of the system 3. An oxidizer, such as air, may be introduced through inlet 8 into the oxidation zone 5 to cause oxidation and re-generation of the oxygen transfer agent. The exothermic heat of oxidation resulting from the re-generation of the oxygen transfer agent may then be transferred through the walls of a heat exchanger in the form of a coil 19 within the oxidation zone 5. A stream introduced into the coil 19 through inlet 15 may include fluids that may result in the endothermic conversion of the contents of the stream. For example, the stream may comprise water resulting in the production of steam from outlet 17. Alternatively, the coil 19 may be a pyrolysis coil and the stream flowing through the coil 19 may comprise ethane resulting in ethylene exiting the outlet 17. Any re-generated oxygen transfer agents may be conveyed back to the oxidation zone 4 via line 11.

The placement of the coils within the reaction zone is particularly beneficial because of the effective heat transfer from the hot oxygen transfer agents through the walls of the coil. The exothermic heat of re-oxidation of the oxygen transfer agents is used to provide the heat of reaction for converting, for example, water to steam or the pyrolysis of ethane to ethylene and other valuable products. In the case of pyrolysis, systems according to the present invention may feed any evolved hydrogen from the pyrolysis coil to the reduction zone of the system to reduce the oxygen transfer agent within the reduction zone.

By using a flameless combustion redox loop to supply heat to endothermic reactions in the systems and processes according to the present invention:

Carbon dioxide and NOx emissions may be essentially eliminated; and

Very high heat transfer rates between the hot solid oxygen transfer reagents through the coils in the oxidizing zone may allow for shorter gas contact times within the coils. Therefore, at the same conversion level of ethane, the amount of internal wall coke formation will be less. This will extend the cycle life of pyrolysis tubes, allowing for more time on stream and less time when the pyrolysis tubes are not producing olefins because carbon is being burned out of the tube.

Figure 2B:
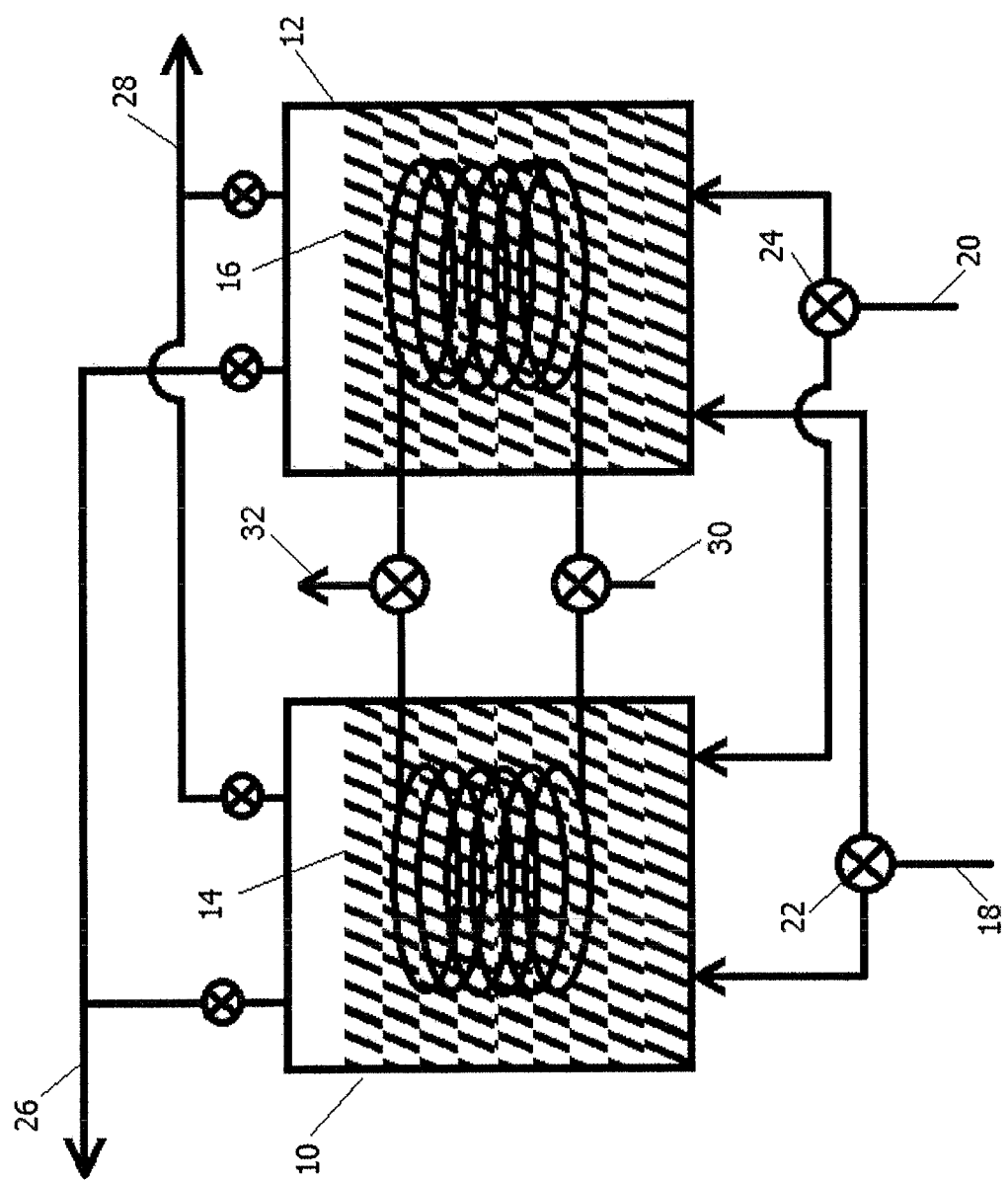
FIG. 2B is a schematic of a dual fixed bed reactor system according to one embodiment of the present invention.

Furthermore, when equation 16 is sufficiently exothermic, reactor conditions may be adjusted such that equation 2 occurs in parallel to equation 15 whereby hydrogen may also be produced from the dehydrogenation of hydrocarbons in the reactor. According to another embodiment of the present invention illustrated in FIG. 2B, two fixed-bed reactors 10, 12 are at least partially filled with a solid oxygen transfer agent 14, 16. A hydrocarbon feed line 18 for delivering a hydrocarbon, such as ethane for example, includes a valve 22 to selectively direct the hydrocarbon feed to either the first reactor 10 or the second reactor 12. If the first reactor 10 is selected, the hydrocarbon will pass through the layer of oxygen transfer agent 14, which promotes an ODH reaction, resulting in a product stream containing an unsaturated hydrocarbon, such as ethene, and water that exits the first effluent line 26. During this process in the first reactor 10, the oxygen transfer agent 14 is reduced over time. In order to regenerate the agent, the feed stream is diverted through valve 22 to the second fixed bed reactor 12, and an oxygen-containing gas stream, such as air, from feed line 20 is fed through valve 24 to the first reactor 10. The oxygen-containing gas oxidizes the oxygen transfer agent 14, and the oxygen-depleted product gas exits effluent stream 28. The exothermic heat of oxidation of the oxygen transfer agent 14 may be utilized to heat a coil 34. A stream is selectively fed through the coil 34 via an inlet 30 having a corresponding valve. The stream may contain water, so that the exothermic heat of oxidation of the oxygen transfer agent 14 produces steam that exits the coil 34 via an outlet/valve 32. Alternatively, the coil 34 may by a pyrolysis coil, so that ethane may be fed via inlet/valve 30 for pyrolytic conversion to ethylene.

As the oxygen transfer agent 14 in the first reactor 10 is being regenerated through oxidation, the second reactor 12 is now producing the unsaturated hydrocarbon that exits the effluent stream 26. Upon reaching the point where regeneration of the oxygen transfer agent 16 in the second reactor 12 is necessary, the hydrocarbon feed and oxygen containing gas feeds may be switched using the valves 22, 24. Similarly the valves 30, 32 may also be switched to divert the stream to coil 36 so that the exothermic heat of oxidation oxygen transfer agent 16 may be used for endothermic conversion of the contents of the stream. This arrangement provides a continuous production of unsaturated hydrocarbon, as well as continuous oxygen transfer agent regeneration. The systems according to the present invention may be run in lean phase, dense phase particle transport, or include a free-falling bed, for example. The reactors in the systems according to various embodiments of the present invention are not limited by the fluidization regime employed in either the hydrocarbon oxidation or re-oxidation reactors.

By coupling exothermic oxidative dehydrogenation with endothermic pyrolysis, systems according to the present invention may:
Lower the overall exotherm of the ODH reaction and thereby make temperature control of the reaction easier and less costly; and
Increase the selectivity of the desired dehydrated hydrocarbon products and decrease unwanted oxidation products, such as carbon dioxide and carbon monoxide.

The systems according to the present invention also have the ability to adjust the hydrogen to water product balance to better meet market needs or the effectiveness of downstream product separation equipment. For example, in the system 3 of FIG. 2A, the by-product water exiting outlet 7 may be increased compared to hydrogen exiting outlet 17 by:
increasing the oxygen transfer agent circulation rate relative to feed 6 to the reduction zone 4,
increasing the reaction rate in the reduction zone 4 compared to the rate of pyrolysis in the coil 19,
circulating oxygen transfer agents with higher amounts of transferable oxygen per weight of catalyst,
increasing the fluid density within the reduction zone, and
lowering the temperature in the oxidation zone 5 generated by the heat of oxidation of the oxygen transfer agent.

Alternatively, the by-product water exiting outlet 7 may be decreased compared to hydrogen exiting outlet 17 by:
decreasing the oxygen transfer agent circulation rate relative to the feed 6 to the reduction zone 4,
decreasing the reaction rate in reduction zone 4 compared to the rate of pyrolysis in coil 19,
circulating oxygen transfer agents with lower amounts of transferable oxygen per weight of catalyst,
increasing the heat capacity of the circulating oxygen transfer agent,
decreasing the fluid density within the reduction zone, and
increasing the temperature in the oxidation zone 5 generated by the heat of oxidation of the oxygen transfer agent.

The reaction pressure in the reactors should be optimized to produce the highest yield of the desired oxidation products. Typical pressures of operation are between 0.1 and 20 atmospheres and more preferably between 1 and 15 atmospheres. The preferred temperature for reaction in the reactor is 400° to 1,000° C. A more narrow operating range of 500-950° C. may be effective depending on the type and amount of promoters included with the oxygen transfer agent. In addition, it may be beneficial to run the process at elevated pressures depending on the promoter material. The temperature and pressure should also be selected to allow for safe operation.

In yet another embodiment of the present invention, the above-described systems may further include the introduction of gas phase promoters into the zones or vessels of the system that facilitate the desired reactions of Equation (6). The addition of gas phase promoters may greatly enhance the selectivity of the desired ODH products when used with oxygen transfer agents of the present invention. The gas phase promoters may also result in higher activity and extend the useful life of the oxygen transfer agents. Various gas phase promoters include, but are not limited to, gas phase water, steam, $CO_2$, halide gases (such as chlorine, bromine, or fluorine), hydrogen halides (such as HCl, HBr, and HF), and sulfur containing gases such as hydrogen sulfide, oxides of sulfur, and organo-sulfur compounds.

The oxygen transfer agents of the present invention may be used to convert various forms of sulfur containing natural gas, which include, but are not limited to, biogas shale gas, associated gas from oil & gas production, coal gas, or any other form of methane containing gas that also contains some form of sulfur, either organic or inorganic sulfur, to higher hydrocarbons. The oxidation of $H_2S$ contained in the natural gas into $SO_2$ and $SO_3$ has been found to be synergistically beneficial for $CO_2$ sequestration, selectivity to $C^{2+}$ products, and useful life of the oxygen transfer agent. Generally, all sulfur in the feed provided to a reactor according to an embodiment of the present invention is converted to $SO_2$, $SO_3$, or a mixture of the two sulfur gases.

Compared to current systems that utilize platinum-based materials to produce unsaturated hydrocarbons, systems according to various embodiments of the present invention advantageously generate low amounts of NOx. Systems that utilize platinum-based catalysts generally require high temperature fuel combustion or de-coking to promote the generation of unsaturated hydrocarbons. High temperatures often lead to NOx production, unless the nitrogen is removed from the feed gases used to maintain combustion in the furnaces. NOx production in these platinum-based systems may be avoided, but only by using expensive pure oxygen feed streams. The exotherm associated with the ODH reactions performed using oxygen transfer agents according to the present invention are relatively low compared to furnace temperatures and therefore, generate little NOx. Thus, systems and methods according to the present invention offer more environmentally friendly and less expensive alternatives to present day processes. The effluent produced by the reactor of the present invention may comprise unconverted hydrocarbons as well as some lower value products, such as carbon dioxide and carbon monoxide that may also be formed at low concentrations. Additional components of the effluent may include oxygenated hydrocarbons, such as alcohols, which are formed in preference to the production of carbon monoxide or carbon dioxide, resulting in an effluent from the reactor with a higher molar concentration of oxygenated hydrocarbons than carbon monoxide or carbon dioxide. It is within the scope of the present invention to recycle the effluent. Similarly, lower value products, such as carbon oxides and water, may be removed from the effluent prior to further treatment.

Preferably, further downstream processes include separation methods in order to isolate polymer grade olefins. For example, ethylene fractionation may include one or more driers in order to remove water prior to feeding the dried product to a distillation column. The distillation column preferably includes several stages to provide a highly pure polymer grade ethylene product. The polymer grade olefins may then be sold as raw materials for the production of higher molecular weight products by oligomerization. Numerous catalysts and processes are known for the oligomerization of olefins generally, and of ethylene particularly, all of which may be employed for converting the polymer grade olefins made according to the various methods of the present invention to higher molecular weight products. For example, phosphoric acid supported on a kieselguhr base has been widely used for making polymer gasoline (i.e., olefinic hydrocarbon liquids within the gasoline boiling range) from refinery gases. Other catalysts which have been employed for similar purposes include the oxides of cobalt, nickel, chromium, molybdenum and tungsten on supports such as alumina, silica-alumina, kieselguhr, carbon and the like. Higher hydrocarbon products of interest may include aviation fuels, kerosene, or intermediate refining streams.

Without intending to limit the scope of the claimed invention, most oligomerization catalysts may be classified in one of two general categories: metal catalysts and acid catalysts. They may also be classified as heterogeneous (solid) catalysts or homogeneous (liquid-phase) catalysts. Examples of metal catalysts that may be used in a process according to the present invention for oligomerization of unsaturated hydrocarbons, include nickel (note that these catalysts require a donor ligand and a Lewis acid), palladium, chromium, cobalt, titanium, tungsten, and rhenium. Examples of acid catalysts include phosphoric acid and acid catalysts based on alumina. Other acid catalysts that may be used in the present invention are silaceous, crystalline molecular sieves. Such silica-containing crystalline materials include materials which contain, in addition to silica, significant amounts of alumina, and generally known as "zeolites", i.e., crystalline aluminosilicates. Silica-containing crystalline materials also include essentially aluminum-free silicates. These crystalline materials are exemplified by crystalline silica polymorphs (e.g., silicalite and organosilicates), chromia silicates (e.g., CZM), ferrosilicates and galliosilicates, and borosilicates. Crystalline aluminosilicate zeolites are best exemplified by ZSM-5, ZSM-11, ZSM12, ZSM-21, ZSM-38, ZSM-23, and ZSM-35.

Metal oligomerization catalysts in general are more sensitive to feed impurities, (e.g., water, carbon monoxide, dienes, etc.) than are the acid catalysts. Although homogeneous, metal catalysts are quite active, the need for dry feeds, solvents, and other measures to prevent catalyst deactivation and precipitation is disadvantageous and suggests an obvious advantage to supported, heterogeneous, metal catalyst. Homogeneous acid catalysts are effective but, are also corrosive and tend to form two liquid-phase systems with the non-polar hydrocarbon oligomerization products. Considering the foregoing observations, heterogeneous acid catalysts are the preferred catalyst for use in the oligomerization step of the process according to the present invention. Of the heterogeneous acid catalysts, acid zeolites are especially preferred, particularly zeolites of the ZSM-type and borosilicates.

While preferred embodiments of the invention have been shown and described herein, it will be understood that such embodiments are provided by way of example only. Numerous variations, changes, and substitutions will occur to those skilled in the art without departing from the spirit of the invention. Accordingly, it is intended that the appended claims cover all such variations as fall within the spirit and scope of the invention.

What is claimed is:

1. A system for promoting endothermic conversions comprising:
    a) a first portion defining a first inner volume at least partially filled with an oxygen transfer agent;
    b) a first supply containing one or more of hydrogen and a saturated hydrocarbon fluidly connected to a first inlet of the first inner volume;
    c) a first outlet conveying one or more of carbon dioxide, water, and an unsaturated hydrocarbon from the first inner volume;
    d) a second portion and a heat exchanger within the second portion, the second portion defining a second inner volume at least partially filled with reduced oxygen transfer agent, the heat exchanger defining a third inner volume segregated from the second inner volume;
    e) a second supply containing an oxidizing agent fluidly connected to a second inlet to the second inner volume; and
    f) a third supply fluidly connected to the third inner volume, wherein the third supply contains a saturated hydrocarbon and, optionally, water;
    wherein the heat exchanger is configured to transfer heat resulting from the oxidation of the reduced oxygen transfer agent in the second inner volume to the third inner volume and the heat from the oxidation of the reduced oxygen transfer agent results in endothermic conversion of the saturated hydrocarbon in the third inner volume to an unsaturated hydrocarbon; and
    wherein at least one of condition i) or condition ii) is met:
        i) the first supply additionally contains a sulfur containing gas; ii) the oxidizing agent is comprised of at least one oxide of sulfur.

2. The system of claim 1 further comprising a conveying means for transporting reduced oxygen transfer agent from the first portion to the second portion and oxidized oxygen transfer agent from the second portion to the first portion providing the heat of reaction for the endothermic conversion of the saturated hydrocarbon.

3. The system of claim 1, wherein the oxygen transfer agent comprises at least one material capable of supplying oxygen and promoting a reaction according to Equation (1) and the at least one material has a heat of reduction less than an exothermic heat of oxidation, wherein Equation (1) is

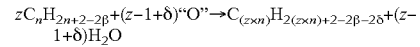

where z=the number of reacting molecules; n=the number of atomic units in the reacting molecule; β=the degree of unsaturation where the value is zero for single bonds, one for double bonds and molecular rings, and two for triple bonds; and δ=the change in the degree of unsaturation.

4. The system of claim 3, wherein the oxidation of the oxygen transfer agent is exothermic.

5. The system of claim 3, wherein the oxygen transfer agent further comprises a second material having a thermal effusivity greater than 3,500 $W \cdot s^{0.5}/m^2$-K.

6. The system of claim 3, wherein the oxygen transfer agent further comprises a second material having a thermal effusivity greater than 10,000 $W \cdot s^{0.5}/m^2$-K.

7. The system of claim 1, wherein the oxygen transfer agent comprises at least one material having a thermal effusivity greater than 3,500 $W \cdot s^{0.5}/m^2$-K.

8. The system of claim 1, wherein the oxygen transfer agent comprises at least one material having a thermal effusivity greater than 10,000 $W \cdot s^{0.5}/m^2$-K.

9. The system of claim 1, wherein the one or more of carbon dioxide, water, and unsaturated hydrocarbon conveyed by the first outlet is the product of oxidative dehydrogenation of the saturated hydrocarbon of the first supply.

10. The system of claim 1, wherein the oxidizing agent comprises oxygen.

11. The system of claim 1, wherein the heat exchanger is in the form of a pyrolysis coil.

12. The system of claim 1, wherein the first supply containing the saturated hydrocarbon comprises a compound according to Formula (1)

$$C_nH_{2n+2-2\beta} \qquad \text{(Formula (1))}$$

where n=the number of atomic units in the reacting molecule; β=the degree of unsaturation where the value is zero for single bonds, one for double bonds and molecular rings, and two for triple bonds.

* * * * *